US012717763B2

(12) United States Patent
Kottler et al.

(10) Patent No.: US 12,717,763 B2
(45) Date of Patent: Aug. 25, 2026

(54) DATA DISCREPANCY ANALYSIS USING MACHINE LEARNING MODELS

(71) Applicant: RADIOLOGY PARTNERS, INC., El Segundo, CA (US)

(72) Inventors: Nina Kottler, San Diego, CA (US); Bartosz Brewinski, Mississauga (CA); Kelly Denney, Hilliard, OH (US); Telford Berkey, London, OH (US); Tuguldur Sukhbold, Dublin, OH (US); Josiah Walton, St. Louis, MO (US)

(73) Assignee: RADIOLOGY PARTNERS, INC., El Segundo, CA (US)

( * ) Notice: Subject to any disclaimer, the term of this patent is extended or adjusted under 35 U.S.C. 154(b) by 36 days.

(21) Appl. No.: 18/068,870

(22) Filed: Dec. 20, 2022

(65) Prior Publication Data

US 2024/0202170 A1 Jun. 20, 2024

(51) Int. Cl.
*G06F 16/215* (2019.01)
*G06F 16/23* (2019.01)
(Continued)

(52) U.S. Cl.
CPC ........ *G06F 16/215* (2019.01); *G06F 16/2365* (2019.01); *G06F 16/258* (2019.01); *G16H 30/20* (2018.01)

(58) Field of Classification Search
None
See application file for complete search history.

(56) References Cited

U.S. PATENT DOCUMENTS 9,317,810 B2 4/2016 Rigdon
9,542,481 B2 1/2017 Halter
(Continued)

FOREIGN PATENT DOCUMENTS

WO 2021212063 A1 10/2021

OTHER PUBLICATIONS

F. J. Garcia-Penalvo, et al., "Application of Artificial Intelligence Algorithms Within the Medical Context for Non-Specialized Users: the CARTIER-IA Platform", International Journal of Interactive Multimedia and Artificial Intelligence, vol. 6, N° 6, Published May 13, 2021, 8 pp.

(Continued)

*Primary Examiner* — Neveen Abel Jalil
*Assistant Examiner* — John J Morris
(74) *Attorney, Agent, or Firm* — Konrad, Raynes, Davda & Victor, LLP; Janaki K. Davda

(57) ABSTRACT

Provided are a computer program product, a system, and a computer-implemented method for performing data discrepancy analysis. Data is received from a plurality of source data systems. The data is analyzed to identify a data discrepancy of a data field. A recommendation is generated that indicates whether the data discrepancy is fixable. In response to the recommendation indicating that the data discrepancy is fixable, the data discrepancy is fixed by modifying a value of the data field, and the data is routed to a first downstream system service that does not rely on the data field and to a second downstream system service that does rely on the data field. In response to the recommendation indicating that the data discrepancy is not fixable, the data is routed to the first downstream system service, while the second downstream system service is disabled.

20 Claims, 10 Drawing Sheets

(51) Int. Cl.
*G06F 16/25* (2019.01)
*G16H 30/20* (2018.01)

(56) References Cited

U.S. PATENT DOCUMENTS

| | | | | |
|---|---|---|---|---|
| 11,204,961 | B1 * | 12/2021 | Farber | H04L 67/61 |
| 11,416,472 | B2 | 8/2022 | Godden | |
| 12,174,821 | B2 * | 12/2024 | Shanbhag | G06F 16/287 |
| 2014/0379718 | A1 * | 12/2014 | Halter | G16H 30/40<br>707/738 |
| 2018/0253669 | A1 | 9/2018 | Thunoli | |
| 2019/0108313 | A1 * | 4/2019 | Jarrett | G16H 40/67 |
| 2020/0334566 | A1 * | 10/2020 | Vianu | G06N 3/084 |
| 2021/0109915 | A1 * | 4/2021 | Godden | G16H 10/60 |
| 2021/0398024 | A1 * | 12/2021 | Pargunarajan | G06N 20/00 |
| 2022/0058193 | A1 * | 2/2022 | Smith | G06F 16/2465 |
| 2023/0315993 | A1 * | 10/2023 | Nieborowski | G06F 16/35<br>704/9 |
| 2023/0403588 | A1 * | 12/2023 | Kumar | H04L 41/16 |
| 2024/0086380 | A1 * | 3/2024 | Vittal | G06F 16/215 |
| 2024/0152493 | A1 * | 5/2024 | Goddijn | G06F 16/254 |

OTHER PUBLICATIONS

T.M. Godinho, et al., “ETL Framework for Real-Time Business Intelligence over Medical Imaging Repositories”, Journal of Digital Imaging (2019), Jan. 31, 2019, 10 pp.

“DICOM Tags”, DICOM Library, 47 pp., [online][retrieved Dec. 1, 2022] https://www.dicomlibrary.com/dicom/dicom-tags.

* cited by examiner

DATA DISCREPANCY ANALYSIS USING MACHINE LEARNING MODELS

BACKGROUND OF THE INVENTION

1. Field of the Invention

The present invention relates to a computer program product, a system, and a computer-implemented method for performing data discrepancy analysis.

2. Description of the Related Art

Medical software, deploying machine learning and artificial intelligence algorithms, is used to assist medical professionals with preparing patient reports, including assisting with billing and reimbursement, and recommending treatments and courses of action. Medical software utilizing machine learning and artificial intelligence is also provided to assist radiologists in preparing patient reports concerning imaging examinations. Machine learning has also been used to improve medical descriptions to assist with billing and insurance reimbursements.

However, the quality of input data that the medical software receives impacts the output. The medical software may receive input of data in accordance with Health Level Seven (HL7) international standards for sharing data between healthcare providers and data in accordance with Digital Imaging and Communications in Medicine (DICOM) standards for sharing medical images and related data between healthcare facilities. There may be data discrepancies in this input data.

There is a need in the art for improved techniques for identifying the discrepancies in the input data and disabling one or more programs that depend on the input data having discrepancies. There is also a need in the art for improved techniques for fixing the discrepancies that may be fixed.

SUMMARY

An embodiment may comprise a computer program product, a system, and a computer-implemented method for performing data discrepancy analysis. Data is received from a plurality of source data systems. The data is analyzed to identify a data discrepancy of a data field. A recommendation is generated that indicates whether the data discrepancy is fixable. In response to the recommendation indicating that the data discrepancy is fixable, the data discrepancy is fixed by modifying a value of the data field, and the data is routed to a first downstream system service that does not rely on the data field and to a second downstream system service that does rely on the data field. In response to the recommendation indicating that the data discrepancy is not fixable, the data is routed to the first downstream system service that does not rely on the data field, while the second downstream system service that does rely on the data field is disabled.

In further embodiments, the data from the plurality of source data systems is analyzed to identify common data configurations.

In further embodiments, the data from the plurality of source data systems is aggregated and standardized.

In further embodiments, a discrepancy dashboard is provided, where the discrepancy dashboard displays common data set configurations and indicates which of the plurality of source data systems are deviating from the common data set configurations.

In further embodiments, the data discrepancy comprises one of a missing value and an incorrect value.

In further embodiments, one or more machine learning models are used to identify the data discrepancy, generate the recommendation, and determine that the second downstream system service is to be disabled.

In further embodiments, a first source data system of the plurality of source data systems comprises first data in accordance with Health Level Seven (HL7) international standards for sharing the first data between healthcare providers, and where a second source data system of the plurality of source data systems comprises second data in accordance with Digital Imaging and Communications in Medicine (DICOM) standards for sharing medical images and related data between healthcare facilities.

DETAILED DESCRIPTION

Figure 1:
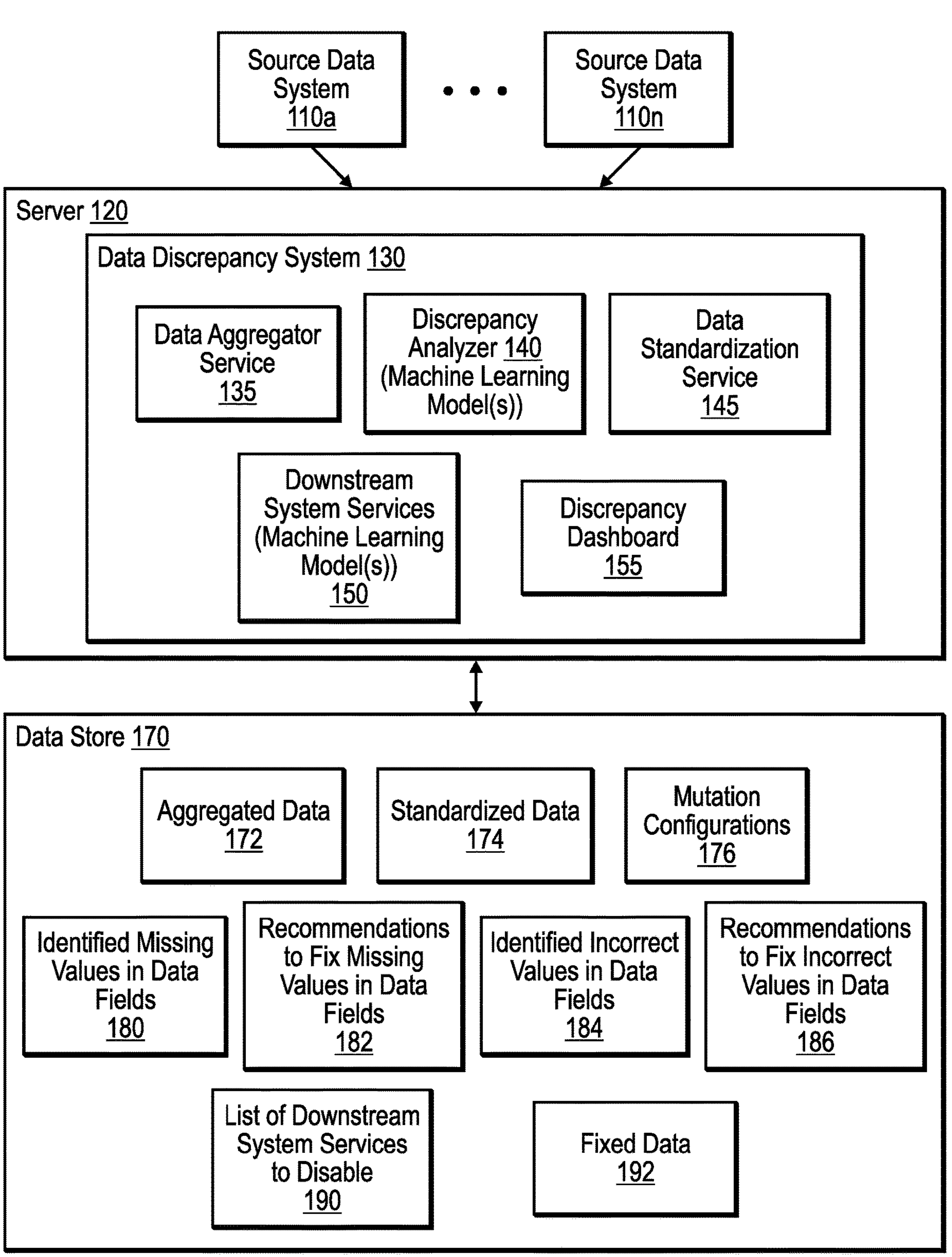
FIG. 1 illustrates an embodiment of a computing environment in which embodiments are implemented.

FIG. 1 illustrates an embodiment of a computing environment in which embodiments are implemented. A server 120 is coupled to source data systems 110*a* . . . 110*n*. The server 120 is also coupled to a data store 170. With embodiments, there may be one or more source data systems 110*a* . . . 110*n*.

The source data systems 110*a* . . . 110*n* may provide data in accordance with HL7 standards and/or data in accordance with DICOM standards. The source data systems 110*a* . . . 110*n* may also provide data in accordance with other standards. The data has data fields. Although examples herein refer to clinical or medical data and images, the source data systems 110*a* . . . 110*n* may provide other types of data. One or more data fields of the data from the source data systems 110*a* . . . 110*n* may have data discrepancies (e.g., missing values in data fields or incorrect values in data fields). A data field having incorrect information may be referred to as “dirty” data (or as a dirty data field). Once the incorrect information in the data has been fixed, the resulting data field may be referred to as “clean” data (or as a clean data field).

The server 120 includes a data discrepancy system 130. The data discrepancy system 130 includes a data aggregator service 135, a discrepancy analyzer 140 (using one or more machine learning models), a data standardization service 145, downstream system services 150 (using one or more machine learning models), and a discrepancy dashboard 155.

With embodiments, the downstream system services 150 may be services, applications, modules (e.g., AI modules), algorithms, etc.

In certain embodiments, the discrepancy analyzer 140 uses a machine learning model. In certain embodiments, the input to the machine learning model of the discrepancy analyzer 140 is the source data (e.g., data in accordance with HL7 standards and/or data in accordance with DICOM standards) that includes one or more data fields with data discrepancies (i.e., missing values or incorrect values), and the output of the machine learning model of the discrepancy analyzer 140 are recommendations of correct values for missing values or incorrect values in data fields. In certain embodiments, the recommendations are predictions of the values that are most likely to fix the data.

In certain embodiments, the output of the machine learning model of the discrepancy analyzer 140 also indicates which downstream system services 150 are to receive the data and which downstream system services 150 are to be disabled (and so not to receive the data) based on whether the recommendations indicate that the missing values or the incorrect values in the data fields are fixable. With embodiments, by not sending the data to a particular downstream system service 150, the downstream system service 150 may be said to be disabled as it does not process that data. With other embodiments, the downstream system service 150 is actively turned off.

One or more of the downstream system services 150 may be implemented with machine learning models. For example, a downstream system service 150 may be implemented with a machine learning model trained to look for certain abnormalities in the data (e.g., in a Computerized Tomography (CT) scan data or in mammogram data). The machine learning model of the downstream system service 150 may expect certain specific data fields to be present in the source data, and if those data fields are not present, the machine learning model of the downstream system service 150 determines that it will not process the data and that the data is not to be sent to one or more particular downstream models that also expect those data fields. In certain embodiments, the input to the machine learning model of the downstream system service 150 is the fixed data 192 output by the data standardization service 145, and the output of the machine learning model are indications of which other downstream system services 150 are to receive the fixed data 192 and which other downstream system services 150 are not to receive the fixed data 192. In this manner, one or more downstream system services 150 that depend on particular data fields that are not in the fixed data 192 are disabled (e.g., turned off or do not receive the fixed data 192 so they do not waste resources processing the fixed data 192).

In certain embodiments, the machine learning model for the discrepancy analyzer 140 may be trained to know what standardized, clean data is, so that when data with discrepancies (e.g., missing values in data fields or incorrect values in data fields) is received, the discrepancy analyzer 140 is able to recognize any discrepancy and describe the deviation to determine whether the discrepancy may be corrected or else returned to the source data system 110*a* . . . 110*n* for updates or recreation of the data (e.g., re-image the patient). In addition, the discrepancy analyzer 140 may be trained to be "performance-conscious", such that the discrepancy analyzer 140 attempts to clean the data in the fastest possible way and uses more time-consuming/resource heavy techniques in response to the most efficient techniques failing to correct the discrepancies.

The data store 170 includes aggregated data 172, standardized data 174, mutation configurations 176, identified missing values in data fields 180, recommendations to fix missing values in data fields 182, identified incorrect values in data fields 184, recommendations to fix the incorrect values in the data fields 186, a list of downstream system services to disable 190, and fixed data 192.

With embodiments, the data discrepancy system 130 provides an analysis mechanism that reviews incoming HL7 and DICOM clinical data and identifies the most common data field configurations (e.g., the common order of the data fields for the data sets). The data discrepancy system 130 identifies where there are data discrepancies between the different source data systems 110*a* . . . 110*n*. The data discrepancy system 130 identifies the most common data field configurations across the source data systems 110*a* . . . 110*n*, which helps to drive future data normalization efforts.

The data discrepancy system 130 may operate to process the data from the source data systems 110*a* . . . 110*n* to output fixed data 192, which is then an input to data routing and analysis of the downstream system services 150.

The data discrepancy system 130 is able to self-optimize to help deal with the data discrepancies. The optimization may be for both the data consistency and for interfacing with machine learning models (e.g., Artificial Intelligence (AI) modules implementing AI algorithms). The data discrepancy system 130 may reduce the deployment implementation (i.e., the time to implement the deployment) based on learning common data field configurations. That is, when the data discrepancy system 130 ingests the data, the data discrepancy system 130 quickly determines whether the data field configuration (i.e., structure) of the data differs from the expected data field configuration of the data. In other words, the data discrepancy system 130 automatically identifies the discrepancies between data sets, and by doing so, avoids a need for manual analysis of the data. In certain embodiments, the data discrepancy system 130 shows the data as normalized (automatically or manually), so that fewer discrepancies are shown.

The data discrepancy system 130 improves the amount of data that may be better processed by the downstream system services 150 to produce a result (without being discarded because a data field is missing a value or has an incorrect value or incorrect format).

In certain embodiments, the data discrepancy system 130 provides AI preparedness analysis by using AI modules to analyze data ingested from different source data systems 110*a* . . . 110*n* (e.g., medical practices), to classify which, if any, data fields from the ingested data are missing values, and which, if any, data fields have incorrect values. The data discrepancy system 130 may also use AI modules to determine whether the missing values and the incorrect values are fixable. Then, based on this knowledge, the data discrepancy system 130 may use AI modules to generate a list of downstream system services to disable 190 that depend on those data fields that have missing values or have incorrect values that are not fixable. The data discrepancy system 130 may also use AI modules to recommend the best remedies to fix the missing values and the incorrect values. For example, the data discrepancy system 130 may detect that what appears to be a missing value is stored in a different data field and automatically fixes the data to store the missing value in the correct data field. As another example, the data discrepancy system 130 may determine that the missing value or the incorrect value of a data field is to be corrected based on historical learning of values in that data field.

Figure 2:
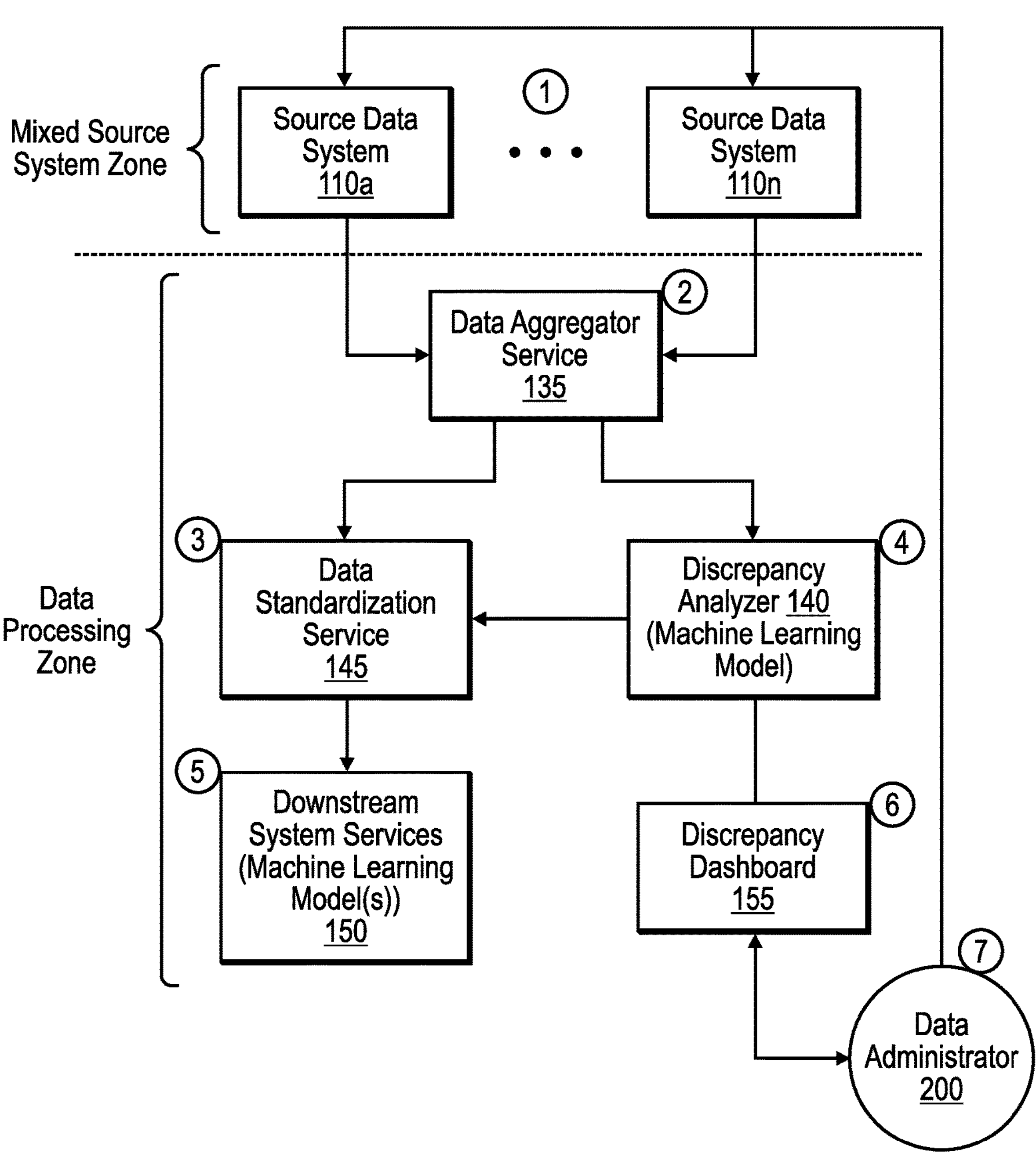
FIG. 2 illustrates an embodiment of a data discrepancy analysis flow in accordance with certain embodiments.

FIG. 2 illustrates an embodiment of a data discrepancy analysis flow in accordance with certain embodiments. The source data systems 110*a* . . . 110*n* form a mixed source system zone, while the data aggregator service 135, the discrepancy analyzer 140, the data standardization service 145, the downstream system services 150, and the discrepancy dashboard 155 form the data processing zone (which may be referred to as a data aggregation zone). In addition, a data administrator 200 may be a human, a computer program, an AI module, etc.

With embodiments, a series of source data systems 110*a* . . . 110*n* feed structured and unstructured data into a central data aggregator service 135. In certain embodiments, each of the source data systems 110*a* . . . 110*n* stores data as data sets with data fields. The source data systems 110*a* . . . 110*n* feed the structured and unstructured data as data sets to the data aggregator service 135. The structured data may be configured differently across the source data systems 110*a* . . . 110*n*. For example, a known data field may exist in both a first data set from a first source data system and a second data set from a second source data system, however, that known data field may be stored within different data fields (i.e., in different locations) within the first data set and the second data set.

In addition, while DICOM header data is structured data, images themselves and the free text within HL7 segments are unstructured data. The discrepancy analyzer 140 analyzes both structured and unstructured data. The HL7 and DICOM standards are flexible about where values are stored (e.g., one source may choose to store a clinical finding in data field xyz, while another source may store the clinical finding in data field abc). Another example of structured data includes database tables with rows and columns, where the columns represent data fields. Other examples of structured data include Extensible Markup Language (XML) data and JavaScript Object Notation (JSON) data. (JavaScript is a registered trademark of Oracle Corporation in the United States and/or other countries).

The data aggregator service 135 collects data sets from the various source data systems 110*a* . . . 110*n*. The data aggregator service 135 combines these data sets from the various source data systems 110*a* . . . 110*n* into a single repository as aggregated data 172.

The data standardization service 145 mutates the aggregated data 172 to ensure that the aggregated data 172 is consistent and that data values are located in standardized (expected) locations. For example, if a disease data value may be expected to be in a particular data field of each data set in the aggregated data, the data standardization service 145 identifies the data sets that do not store the disease data value in the particular data field in the data set and mutates these data sets to ensure that the disease data value is in the expected data field. In various embodiments, the data mutation may be performed based on: pre-configured data mutation rules and/or dynamic mutation configuration input received from the discrepancy analyzer 140. After processing the aggregated data, the data standardization service 145 stores the data as standardized data 174.

The discrepancy analyzer 140 reviews the aggregated data 172 and identifies the most common data field configurations from across the different data sets from the various source data systems 110*a* . . . 110*n*. The discrepancy analyzer 140 detects like (e.g., "similar" or having the same characteristics) data fields across data sets in the aggregated data 172 using machine learning models. These like data fields are then used to determine whether data fields are stored in different locations across data sets that do not adhere to the most common data field configurations across the source data systems 110*a* . . . 110*n*.

Embodiments train different machine learning models used by the discrepancy analyzer 140 when a data field value is missing versus when a data field value is incorrect ("dirty") from the source data systems 110*a* . . . 110*n*. When a data field value is missing, the input to the machine learning model includes the source data (e.g., an HL7 file with data in accordance with HL7 standards and/or a DICOM file with data in accordance with DICOM standards) that includes one or more data fields with missing values. The machine learning model looks at the non-missing values in other data fields, as well as, historically trained knowledge of the typical value found in that data field and attempts to infer what the missing value is depending on which data field value is missing. The output of the machine learning model is the recommendation of the value for the data field with the missing value. On the other hand, when the data field value is incorrect, the input to the machine learning model include the source data (e.g., an HL7 file with data in accordance with HL7 standards and/or a DICOM file with data in accordance with DICOM standards) that includes one or more data fields with incorrect values. The machine learning model looks at which attributes are discrepant compared to the trained machine learning model, as well as, historically trained knowledge of the typical value found in that data field and attempts to infer what the incorrect value is depending on which data field value is incorrect and what value is expected. The output of the machine learning model is a recommendation of how to modify the incorrect values to make the data field value clean.

The discrepancy analyzer 140 dynamically provides mutation configurations 176 as input to the data standardization service 145 when discrepancies between data field configuration is detected. For example, a mutation configuration may indicate: "move value of data field x to data field y for system z". The following is an example of data fields, which may be mutated:

```
{
  sourceSite: "ABC"
  sourceField: "Field_0002"
  targetField: "Field_0003"
}
```

The discrepancy analyzer 140 initiates determining the mutation configurations 176 when configured criteria permits it to do so or after manual input from the data administrator 200. The mutation configurations 176 are provided as input to the data standardization service 145 to mutate data into a more consistent format moving forward.

The downstream system services 150 may rely on data sets to be provided in a consistent format. These downstream system services 150 provide desired functionality. For example, the downstream system services 150 may assist medical professionals with preparing patient reports, including assisting with billing and reimbursement, and recommending treatments and courses of action. As another example, the downstream system services 150 may assist radiologists in preparing patient reports concerning imaging examinations. As a further example, the downstream system services 150 may store the data in a consistent matter and may help review the data. With embodiments, the downstream system services 150 may use machine learning models.

The discrepancy dashboard 155 may be described as a visual interface for the data administrator to review discrepancies in the data sets provided by the source data systems 110*a* . . . 110*n*. The discrepancy dashboard 155 may provide information about the most common data field configurations. The discrepancy dashboard 155 may identify which source data systems 110*a* . . . 110*n* are deviating from the most common data field configurations. The discrepancy dashboard 155 may dynamically display suggested mutation configurations. Then, the discrepancy dashboard 155 may either automatically apply the mutation configurations or enable the data administrator 200 to provide input on which of the mutation configurations are to be applied.

The data administrator 200 has the role of reviewing the quality of the data being ingested into the data processing zone. Based on the quality of the data, the data administrator 200 may permit the data processing zone to self-correct the ingested data via the internal data standardization service 145 or use the information presented in the discrepancy dashboard 155 to retrain or expand training of the discrepancy analyzer 140 or to inform upstream data owners to perform better data field configuration of data coming from the source data systems 110*a* . . . 110*n* so that more consistent data is fed into the data processing zone.

Figure 3:
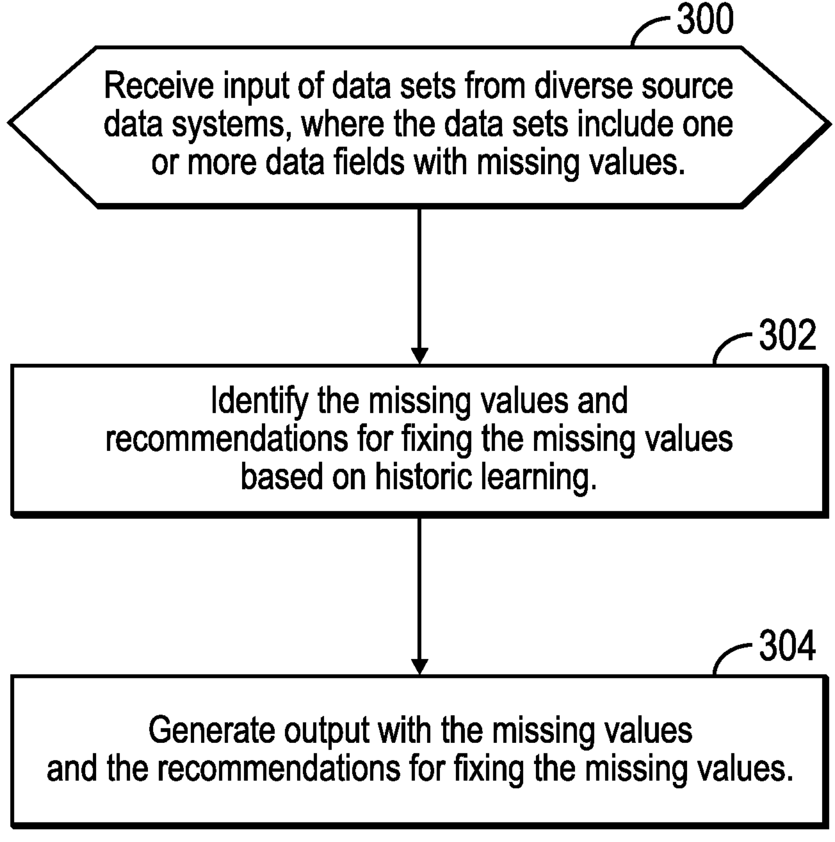
FIG. 3 illustrates, in a flow chart, operations for correcting missing values in accordance with certain embodiments.

FIG. 3 illustrates, in a flow chart, operations for correcting missing values in accordance with certain embodiments. Control begins at block 300 with a machine learning model of the discrepancy analyzer 140 receiving input of data sets from diverse source data systems, where the data sets include one or more data fields with missing values. In block 302, the machine learning model of the discrepancy analyzer 140 identifies the missing values and recommendations for fixing the missing values based on historic learning. In block 304, the machine learning model of the discrepancy analyzer 140 generates output with the missing values and the recommendations for fixing the missing values. With embodiments, the data standardization service 145 applies the recommendations to the data sets to generate fixed data 192. In certain embodiments, one or more of the missing values is not fixable, the recommendation for that missing value indicates that the missing value is not fixable, and the fixed data 192 includes an indication that the missing value is not fixable.

Figure 4:
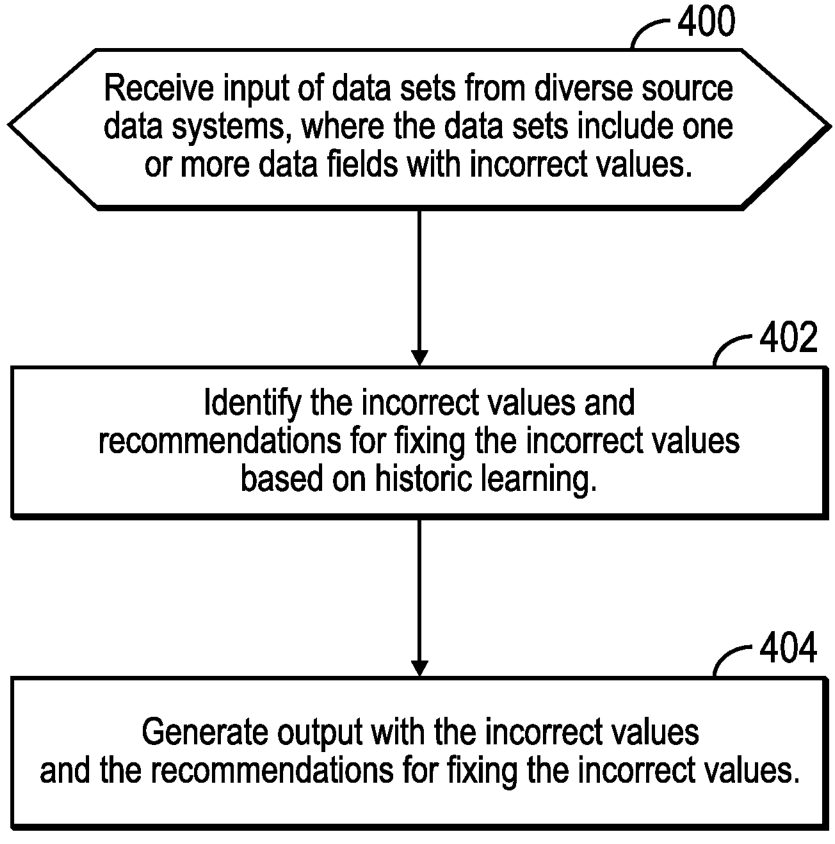
FIG. 4 illustrates, in a flow chart, operations for correcting incorrect values in accordance with certain embodiments.

FIG. 4 illustrates, in a flow chart, operations for correcting incorrect values in accordance with certain embodiments. Control begins at block 400 with a machine learning model of the discrepancy analyzer 140 receiving input of data sets from diverse source data systems, where the data sets include one or more data fields with incorrect values. In block 402, the machine learning model of the discrepancy analyzer 140 identifies the incorrect values and recommendations for fixing the incorrect values based on historic learning. In block 404, the machine learning model of the discrepancy analyzer 140 generates output with the incorrect values and the recommendations for fixing the incorrect values. With embodiments, the data standardization service 145 applies the recommendations to the data sets to generate fixed data 192. In certain embodiments, one or more of the incorrect values is not fixable, the recommendation for that incorrect value indicates that the incorrect value is not fixable, and the fixed data 192 includes an indication that the incorrect value is not fixable.

In certain embodiments, one machine learning model of the discrepancy analyzer 140 process input data sets with both missing values and incorrect values and outputs the recommendations to correct the missing values and the incorrect values.

Figure 5:
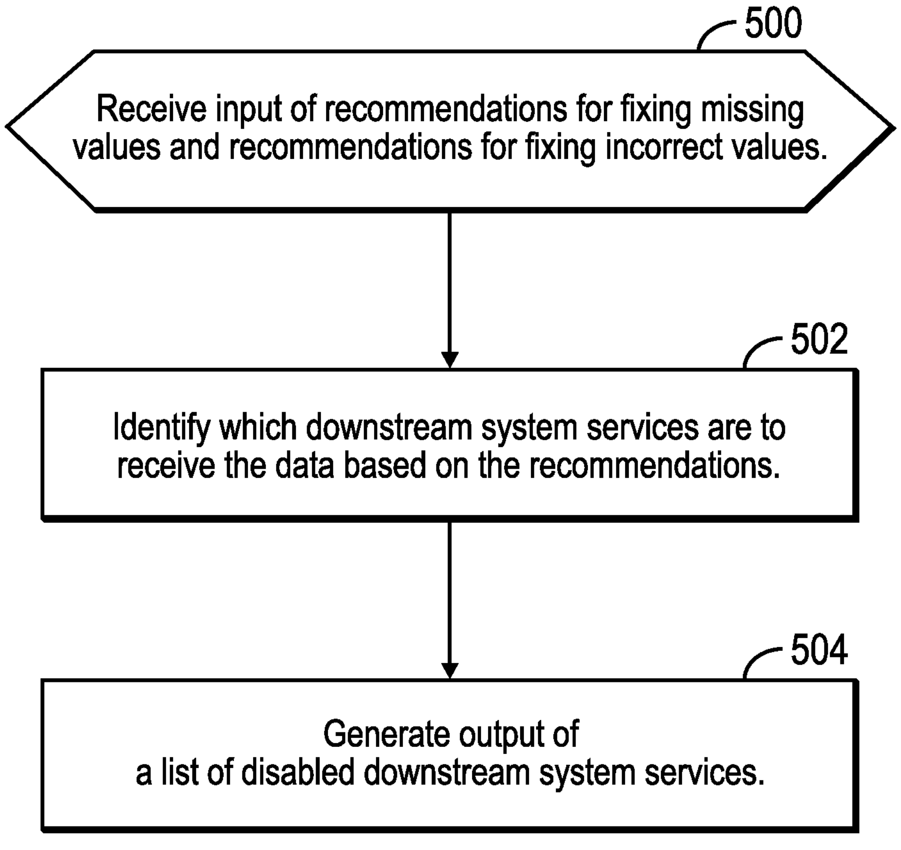
FIG. 5 illustrates, in a flow chart, operations by a discrepancy analyzer for disabling one or more downstream system services in accordance with certain embodiments.

FIG. 5 illustrates, in a flow chart, operations by the discrepancy analyzer 140 for disabling one or more downstream system services in accordance with certain embodiments. Control begins at block 500 with a machine learning model of the discrepancy analyzer 140 receiving input of recommendations for fixing missing values and incorrect values. In block 502, the machine learning model of the discrepancy analyzer 140 identifies which downstream system services 150 are to receive the data based on the recommendations. For example, if the recommendations indicate that values of certain data fields are not fixable, and a particular downstream system service 150 expects that data field, the particular downstream system service 150 is identified as on that will be disabled.

In block 504, the machine learning model of the discrepancy analyzer 140 generates output of a list of downstream system services to disable 190. In certain embodiments, a list of downstream system services to enable (i.e., receive the data) is also output. In certain embodiments, the discrepancy analyzer 140 also disables the downstream services 150 on the list of downstream system services to disable 190.

Figure 6:
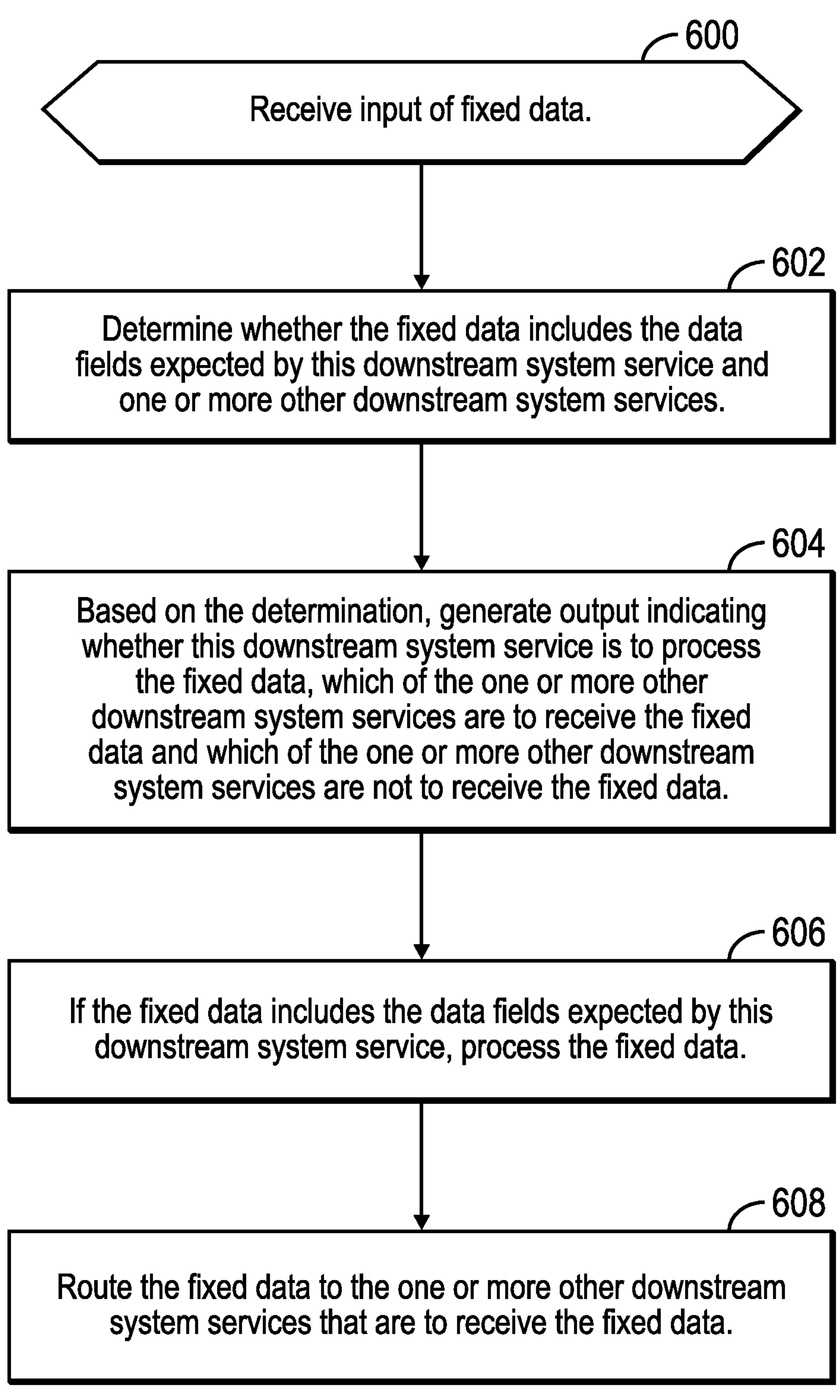
FIG. 6 illustrates, in a flowchart, operations by a downstream system service for disabling one or more downstream system services in accordance with certain embodiments.

FIG. 6 illustrates, in a flowchart, operations by the downstream system service 150 for disabling one or more downstream system services 150 in accordance with certain embodiments. Control begins at block 600 with a downstream system service 150 receiving fixed data 192. In block 602, the machine learning model of a downstream system service 150 determines whether the fixed data 192 includes the data fields expected by this downstream system service 150 and one or more other downstream system services 150. The operation of block 602 takes into consideration that one or more values are not fixable. In block 604, the machine learning model of the downstream system service 150, based on the determination, generates output indicating whether this downstream system service 150 is to process the fixed data 192, which of the one or more other downstream system services 150 are to receive the fixed data 192, and which of the one or more other downstream system services 150 are not to receive the fixed data 192. In block 606, if the fixed data 192 includes the data fields expected by this downstream system service 150, the downstream system service 150 processes the fixed data 192. In block 608, the downstream system service 150 routes the fixed data 192 to the one or more other downstream system services 150 that are to receive the fixed data 192. For example, if a first downstream system service 150 process the data set with fields A, B, and C, and a data value in field C is not fixable, the data set is not routed to the first downstream system service 150. As another example, if a second downstream system service 150 processes the data set with fields A, B, and D, and a data value in field C is not fixable, then the data set is routed to the second downstream system service 150.

Figure 7:
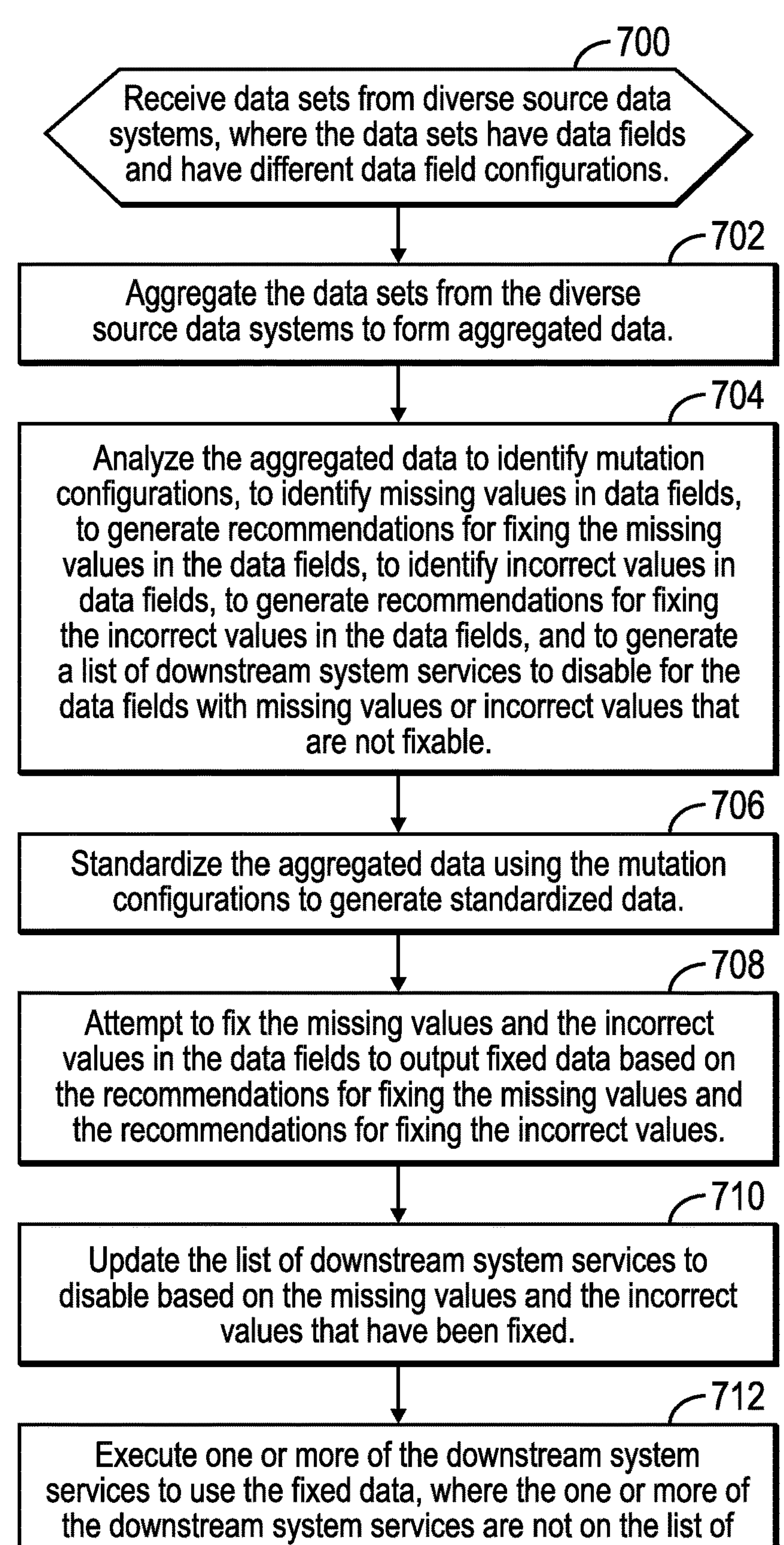
FIG. 7 illustrates, in a flowchart, operations to perform data discrepancy analysis in accordance with certain embodiments.

FIG. 7 illustrates, in a flowchart, operations to perform data discrepancy analysis in accordance with certain embodiments. Control begins at block 700, with the data aggregator service 135 of the data discrepancy system 130 receiving data sets from diverse source data systems, where the data sets have data fields and have different data field configurations. In block 702, the data aggregator service 135 aggregates the data sets from the diverse source data systems to form aggregated data.

In block 704, the discrepancy analyzer 140 of the data discrepancy system 130 analyzes the aggregated data to identify mutation configurations 176, to identify missing values in data fields 180, to generate recommendations for fixing the missing values in the data fields 182, to identify incorrect values in data fields 184, to generate recommendations for fixing the incorrect values in the data fields 186, and to generate a list of downstream system services to disable 190 based on the data fields with missing values or incorrect values that are not fixable. In certain embodiments, the operations of block 704 are performed using machine learning models, such as those described in FIGS. 3, 4, and 5.

With embodiments, the generation of recommendations may be configuration based. For example, for a series of downstream system services 150 that consume data, the configuration may indicate which data each of the downstream system services 150 is expecting. If the discrepancy analyzer 140 identifies that some of the expected data fields are missing in an incoming data set, the discrepancy analyzer 140 may prevent sending that data to the affected consuming downstream system service 150. That way, resources of the downstream system service 150 are not wasted trying to receive/process the incoming data with the missing values or the incorrect values that are not fixable.

In block 706, the standardization service 145 of the data discrepancy system 130 standardizes the aggregated data using the mutation configurations to generate standardized data.

In block 708, the standardization service 145 attempts to fix the missing values and the incorrect values in the data fields to output fixed data 192 based on the recommendations for fixing the missing values and the recommendations for fixing the incorrect values.

In block 710, the standardization service 145 updates the list of downstream system services to disable 190 based on the missing values and the incorrect values that have been fixed.

In block 712, the downstream system services 150 executes one or more of the downstream system services 150 to use the fixed data 192, where the one or more downstream system services 150 are not on the list of downstream system services to disable 190. Executing the one or more of the downstream system services 150 includes sending the fixed data 192 to those one or more downstream system services 150 or making the fixed data 192 accessible to those one or more downstream system services 150.

Figure 8:
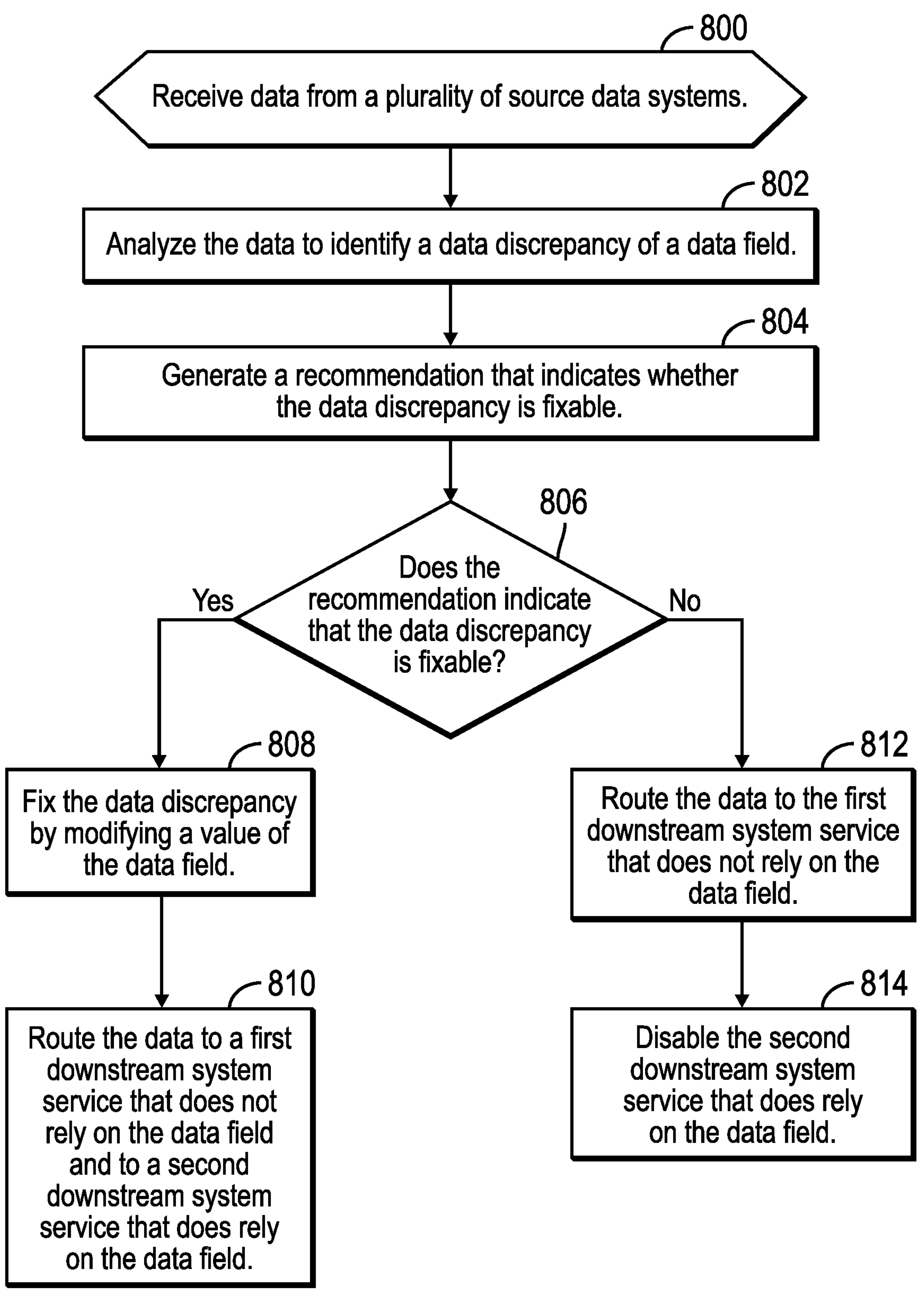
FIG. 8 illustrates, in a flowchart, operations to disable a downstream system service in accordance with certain embodiments.

FIG. 8 illustrates, in a flowchart, operations to disable a downstream system service in accordance with certain embodiments. Control begins at block 800 with the data discrepancy system 130 receiving data from a plurality of source data systems. In block 802, the data discrepancy system 130 analyzes the data to identify a data discrepancy of a data field. In block 804, the data discrepancy system 130 generates a recommendation that indicates whether the data discrepancy is fixable.

In block 806, the data discrepancy system 130 determines whether the recommendation indicates that the data discrepancy is fixable. If so, processing continues to block 808, otherwise, processing continues to block 812.

In block 808, the data discrepancy system 130 fixes the data discrepancy by modifying a value of the data field. In block 810, the data discrepancy system 130 routes the data to a first downstream system service 150 that does not rely on the data field and to a second downstream system service 150 that does rely on the data field.

In block 812, the data discrepancy system 130 routes the data to the first downstream system service 150 that does not rely on the data field. In block 814, the data discrepancy system 130 disables a second downstream system service 150 that does rely on the data field. In certain embodiments, the second downstream service 150 is disabled by being turned off. In certain other embodiments, the second downstream system service 150 disabled as the data is not routed to the second downstream system service 150.

With embodiments, a discrepancy dashboard is provided that displays common data set configurations and indicates which of the plurality of source data systems are deviating from the common data set configurations.

With embodiments one or more machine learning models are used to identify the data discrepancy, generate the recommendation, and determine that the second downstream system service 150 is to be disabled.

Figure 9:
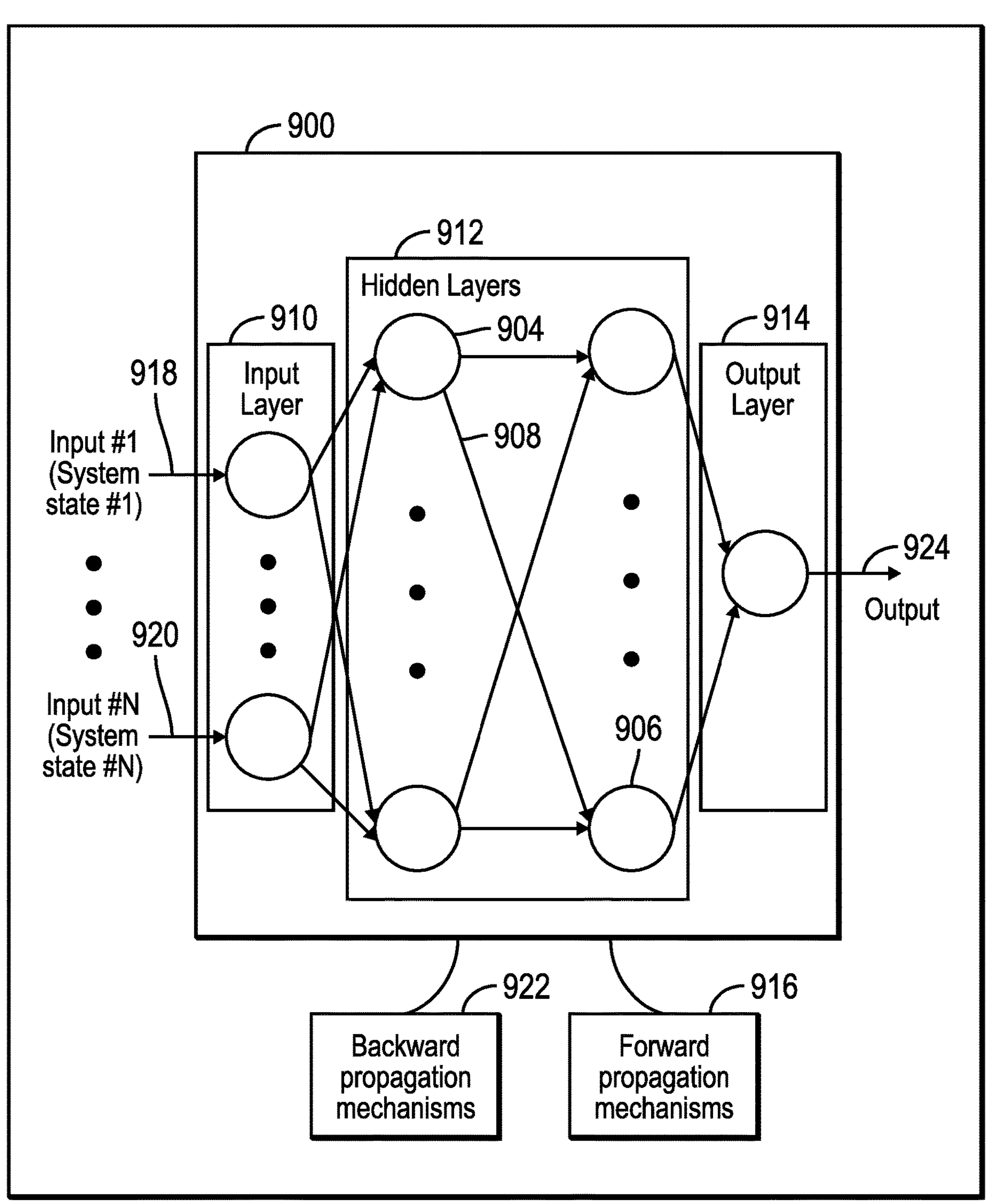
FIG. 9 illustrates, in a block diagram, details of a machine learning model in accordance with certain embodiments.

FIG. 9 illustrates, in a block diagram, details of a machine learning model 900 in accordance with certain embodiments. In certain embodiments, the one or more machine learning models for the discrepancy analyzer and the downstream system services are implemented using the components of the machine learning model 900.

The machine learning model 900 may comprise a neural network with a collection of nodes with links connecting them, where the links are referred to as connections. For example, FIG. 9 shows a node 904 connected by a connection 908 to the node 906. The collection of nodes may be organized into three main parts: an input layer 910, one or more hidden layers 912, and an output layer 914.

The connection between one node and another is represented by a number called a weight, where the weight may be either positive (if one node excites another) or negative (if one node suppresses or inhibits another). Training the machine learning model 900 entails calibrating the weights in the machine learning model 900 via mechanisms referred to as forward propagation 916 and backward propagation 922. Bias nodes that are not connected to any previous layer may also be maintained in the machine learning model 900. A bias may be described as an extra input of 1 with a weight attached to it for a node.

In forward propagation 916, a set of weights are applied to the input data 918 . . . 920 to calculate the output 924. For the first forward propagation, the set of weights may be selected randomly or set by, for example, a system administrator. That is, in the forward propagation 916, embodiments apply a set of weights to the input data 918 . . . 920 and calculate an output 924.

In backward propagation 922 a measurement is made for a margin of error of the output 924, and the weights are adjusted to decrease the error. Backward propagation 922 compares the output that the machine learning model 900 produces with the output that the machine learning model 900 was meant to produce, and uses the difference between them to modify the weights of the connections between the nodes of the machine learning model 900, starting from the output layer 914 through the hidden layers 912 to the input layer 910, i.e., going backward in the machine learning model 900. In time, backward propagation 922 causes the machine learning model 900 to learn, reducing the difference between actual and intended output to the point where the two come very close or coincide.

The machine learning model 900 may be trained using backward propagation to adjust weights at nodes in a hidden layer to produce adjusted output values based on the provided inputs 918 . . . 920. A margin of error may be determined with respect to the actual output 924 from the machine learning model 900 and an expected output to train the machine learning model 900 to produce the desired output value based on a calculated expected output. In backward propagation, the margin of error of the output may be measured and the weights at nodes in the hidden layers 912 may be adjusted accordingly to decrease the error.

Backward propagation may comprise a technique for supervised learning of artificial neural networks using gradient descent. Given an artificial neural network and an error function, the technique may calculate the gradient of the error function with respect to the artificial neural network's weights.

Thus, the machine learning model 900 is configured to repeat both forward and backward propagation until the weights of the machine learning model 900 are calibrated to accurately predict an output.

The machine learning model 900 implements a machine learning technique such as decision tree learning, association rule learning, artificial neural network, inductive programming logic, support vector machines, Bayesian models, etc., to determine the output value 924.

In certain machine learning model 900 implementations, weights in a hidden layer of nodes may be assigned to these inputs to indicate their predictive quality in relation to other of the inputs based on training to reach the output value 924.

With embodiments, the machine learning model 900 is a neural network, which may be described as a collection of "neurons" with "synapses" connecting them.

With embodiments, there may be multiple hidden layers 912, with the term "deep" learning implying multiple hidden layers. Hidden layers 912 may be useful when the neural network has to make sense of something complicated, contextual, or non-obvious, such as image recognition. The term "deep" learning comes from having many hidden layers. These layers are known as "hidden", since they are not visible as a network output.

In certain embodiments, training a neural network may be described as calibrating all of the "weights" by repeating the forward propagation 916 and the backward propagation 922.

In backward propagation 922, embodiments measure the margin of error of the output and adjust the weights accordingly to decrease the error.

Neural networks repeat both forward and backward propagation until the weights are calibrated to accurately predict the output 924.

In certain embodiments, the machine learning model may be refined based on whether the outputted recommendations, once taken, generate positive outcomes.

The present invention may be a system, a method, and/or a computer program product. The computer program product may include a computer readable storage medium (or media) having computer readable program instructions thereon for causing a processor to carry out aspects of the present invention.

The computer program product comprises a computer readable storage medium implemented using standard programming and/or engineering techniques to produce software, firmware, hardware, or any combination thereof. The described operations may be implemented as code or logic maintained in a "computer readable storage medium". The term "code" and "program code" as used herein refers to software program code, hardware logic, firmware, microcode, etc. The computer readable storage medium, as that term is used herein, includes a tangible element, including at least one of electronic circuitry, storage materials, a casing, a housing, a coating, hardware, and other suitable materials. A computer readable storage medium may comprise, but is not limited to, a magnetic storage medium (e.g., hard disk drives, floppy disks, tape, etc.), optical storage (CD-ROMs, DVDs, optical disks, etc.), volatile and non-volatile memory devices (e.g., EEPROMs, ROMs, PROMs, RAMS, DRAMs, SRAMs, Flash Memory, firmware, programmable logic, etc.), Solid State Devices (SSD), computer encoded and readable punch cards, etc. The computer readable storage medium may further comprise a hardware device implementing firmware, microcode, etc., such as in an integrated circuit chip, a programmable logic device, a Programmable Gate Array (PGA), field-programmable gate array (FPGA), Application Specific Integrated Circuit (ASIC), etc. A computer readable storage medium is not comprised solely of transmission signals and includes physical and tangible components. Those skilled in the art will recognize that many modifications may be made to this configuration without departing from the scope of the present invention, and that the article of manufacture may comprise suitable information bearing medium known in the art.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 10:
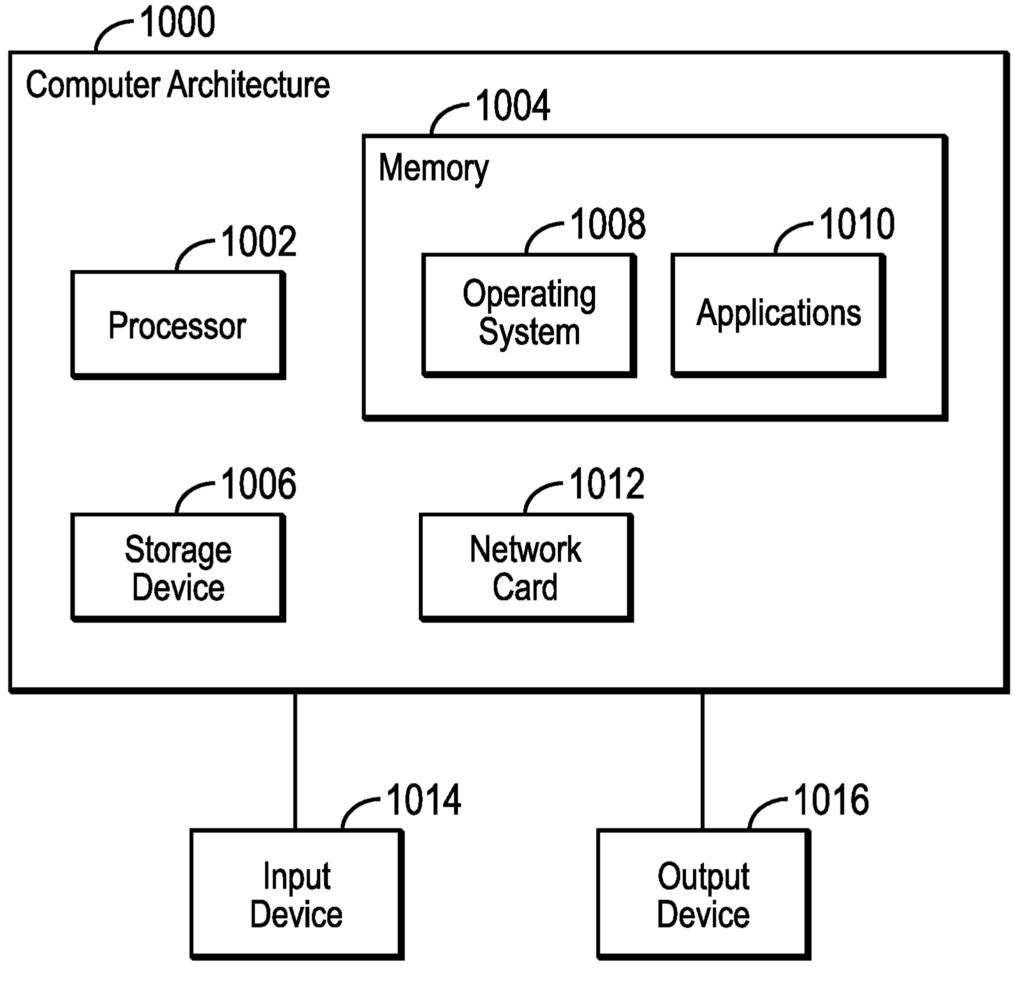
FIG. 10 illustrates a computing environment in which the server of FIG. 1 may be implemented.

The server 120 of FIG. 1 may be implemented in one or more computer systems, having a computer architecture as shown in FIG. 10, and including a processor 1002 (e.g., one or more microprocessors and cores), a memory 1004 (e.g., a volatile memory device), and storage 1006 (e.g., a non-volatile storage, such as magnetic disk drives, solid state devices (SSDs), optical disk drives, a tape drive, etc.). The storage 1006 may comprise an internal storage device or an attached or network accessible storage. Programs, including an operating system 1008 and applications 1010 (i.e., code) stored in the storage 1006 are loaded into the memory 1004 and executed by the processor 1002. In certain embodiments, the applications 1010 may include the data aggregator service 135, the discrepancy analyzer 140, the data standardization service 145, the downstream system services 150, and the discrepancy dashboard 155, and other program components described above. In certain other embodiments, any combination of the data aggregator service 135, the discrepancy analyzer 140, the data standardization service 145, the downstream system services 150, and the discrepancy dashboard 155 may be modules of an application, such as the data discrepancy system 130. The architecture 1000 further includes a network card 1012 to enable communication with the network 16. An input device 1017 is used to provide user input to the processor 1002, and may include a keyboard, mouse, pen-stylus, microphone, touch sensitive display screen, or any other activation or input mechanism known in the art. An output device 1016, such as a display monitor, printer, storage, etc., is capable of rendering information transmitted from a graphics card or other component. The output device 1016 may render the GUIs described with respect to figures and the input device 1014 may be used to interact with the graphical controls and elements in the GUIs described above. The architecture 1000 may be implemented in any number of computing devices, such as a server, mainframe, desktop computer, laptop computer, hand held computer, tablet computer, personal digital assistant (PDA), telephony device, cell phone, etc.

The terms "an embodiment", "embodiment", "embodiments", "the embodiment", "the embodiments", "one or more embodiments", "some embodiments", and "one embodiment" mean "one or more (but not all) embodiments of the present invention(s)" unless expressly specified otherwise.

The terms "including", "comprising", "having" and variations thereof mean "including but not limited to", unless expressly specified otherwise.

The enumerated listing of items does not imply that any or all of the items are mutually exclusive, unless expressly specified otherwise.

The terms "a", "an" and "the" mean "one or more", unless expressly specified otherwise.

Devices that are in communication with each other need not be in continuous communication with each other, unless expressly specified otherwise. In addition, devices that are in communication with each other may communicate directly or indirectly through one or more intermediaries.

A description of an embodiment with several components in communication with each other does not imply that all such components are required. On the contrary a variety of optional components are described to illustrate the wide variety of possible embodiments of the present invention.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features. Thus, other embodiments of the present invention need not include the device itself.

The foregoing description of various embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto. The above specification, examples and data provide a complete description of the manufacture and use of the composition of the invention. Since many embodiments of the invention can be made without departing from the spirit and scope of the invention, the invention resides in the claims herein after appended.

What is claimed is:

1. A computer program product, the computer program product comprising a non-transitory computer readable storage medium having computer readable program code embodied therein that is executable to perform operations, the operations comprising:

receiving data from a plurality of source data systems, wherein the data comprises data fields and includes a first data discrepancy of a first data field and a second data discrepancy of a second data field, wherein the data is from a first source data system of the plurality of source data systems comprising first standards and a second source data system of the plurality of source data systems comprising second standards;

making a first determination for routing the data to a plurality of downstream system services by:

inputting, to a first machine learning model, the data; and receiving, from the first machine learning model, recommendations to fix the first data discrepancy and the second data discrepancy and a list of downstream system services of the plurality of downstream system services to disable based on the first data discrepancy and the second data discrepancy;

fixing the first data discrepancy using one of the recommendations to generate fixed data;

attempting to fix the second data discrepancy using another of the recommendations;

updating the list of downstream system services to remove a first downstream system service from the list based on determining that the first data discrepancy is fixed and that the first downstream system service does not rely on the second data field that cannot be fixed;

disabling a second downstream system service on the list that does rely on the second data field that cannot be fixed; and routing the fixed data to one or more downstream system services that are not on the list, wherein the first downstream system service makes a second determination for routing the fixed data to the plurality of downstream system services by inputting, to a second machine learning model, the fixed data, wherein the second machine learning model determines whether the fixed data includes the data fields expected by one or more other downstream system services and, based on the determination, generates output indicating which of the one or more other downstream system services are to receive the fixed data and which of the one or more other downstream system services are not to receive the fixed data.

2. The computer program product of claim 1, wherein the data from the plurality of source data systems is analyzed to identify one or more mutation configurations.

3. The computer program product of claim 1, wherein the data from the plurality of source data systems is aggregated and standardized.

4. The computer program product of claim 1, wherein the computer readable program code is executable to perform further operations comprising:

providing a discrepancy dashboard, wherein the discrepancy dashboard displays common data set configurations and indicates which of the plurality of source data systems are deviating from the common data set configurations.

5. The computer program product of claim 1, wherein the first data discrepancy comprises one of a missing value and an incorrect value.

6. The computer program product of claim 1, wherein the first standards comprise Health Level Seven (HL7) international standards, and wherein the second standards comprise Digital Imaging and Communications in Medicine (DICOM) standards.

7. The computer program product of claim 1, wherein the first downstream system service forwards the fixed data to the one or more other downstream system services that are to receive the fixed data.

8. A system, comprising:

a processor; and a computer readable storage medium having computer readable program code that when executed by the processor performs operations, the operations comprising:

receiving data from a plurality of source data systems, wherein the data comprises data fields and includes a first data discrepancy of a first data field and a second data discrepancy of a second data field, wherein the data is from a first source data system of the plurality of source data systems comprising first standards and a second source data system of the plurality of source data systems comprising second standards;

making a first determination for routing the data to a plurality of downstream system services by:

inputting, to a first machine learning model, the data; and receiving, from the first machine learning model, recommendations to fix the first data discrepancy and the second data discrepancy and a list of downstream system services of the plurality of downstream system services to disable based on the first data discrepancy and the second data discrepancy;

fixing the first data discrepancy using one of the recommendations to generate fixed data;

attempting to fix the second data discrepancy using another of the recommendations;

updating the list of downstream system services to remove a first downstream system service from the list based on determining that the first data discrepancy is fixed and that the first downstream system service does not rely on the second data field that cannot be fixed;

disabling a second downstream system service on the list that does rely on the second data field that cannot be fixed; and routing the fixed data to one or more downstream system services that are not on the list, wherein the first downstream system service makes a second determination for routing the fixed data to the plurality of downstream system services by inputting, to a second machine learning model, the fixed data, wherein the second machine learning model determines whether the fixed data includes the data fields expected by one or more other downstream system services and, based on the determination, generates output indicating which of the one or more other downstream system services are to receive the fixed data and which of the one or more other downstream system services are not to receive the fixed data.

9. The system of claim 8, wherein the data from the plurality of source data systems is analyzed to identify one or more mutation configurations.

10. The system of claim 8, wherein the data from the plurality of source data systems is aggregated and standardized.

11. The system of claim 8, wherein the operations further comprise: providing a discrepancy dashboard, wherein the discrepancy dashboard displays common data set configurations and indicates which of the plurality of source data systems are deviating from the common data set configurations.

12. The system of claim 8, wherein the first data discrepancy comprises one of a missing value and an incorrect value.

13. The system of claim 8, wherein the first standards comprise Health Level Seven (HL7) international standards, and wherein the second standards comprise Digital Imaging and Communications in Medicine (DICOM) standards.

14. The system of claim 8, wherein the first downstream system service forwards the fixed data to the one or more other downstream system services that are to receive the fixed data.

15. A computer-implemented method comprising operations for:

receiving data from a plurality of source data systems, wherein the data comprises data fields and includes a first data discrepancy of a first data field and a second data discrepancy of a second data field, wherein the data is from a first source data system of the plurality of source data systems comprising first standards and a second source data system of the plurality of source data systems comprising second standards;

making a first determination for routing the data to a plurality of downstream system services by:

inputting, to a first machine learning model, the data; and receiving, from the first machine learning model, recommendations to fix the first data discrepancy and the second data discrepancy and a list of downstream system services of the plurality of downstream system services to disable based on the first data discrepancy and the second data discrepancy;

fixing the first data discrepancy using one of the recommendations to generate fixed data;

attempting to fix the second data discrepancy using another of the recommendations;

updating the list of downstream system services to remove a first downstream system service from the list based on determining that the first data discrepancy is fixed and that the first downstream system service does not rely on the second data field that cannot be fixed;

disabling a second downstream system service on the list that does rely on the second data field that cannot be fixed; and routing the fixed data to one or more downstream system services that are not on the list, wherein the first downstream system service makes a second determination for routing the fixed data to the plurality of downstream system services by inputting, to a second machine learning model, the fixed data, wherein the second machine learning model determines whether the fixed data includes the data fields expected by one or more other downstream system services and, based on the determination, generates output indicating which of the one or more other downstream system services are to receive the fixed data and which of the one or more other downstream system services are not to receive the fixed data.

16. The computer-implemented method of claim 15, wherein the data from the plurality of source data systems is analyzed to identify one or more mutation configurations.

17. The computer-implemented method of claim 15, wherein the data from the plurality of source data systems is aggregated and standardized.

18. The computer-implemented method of claim 15, wherein the operations further comprise:

providing a discrepancy dashboard, wherein the discrepancy dashboard displays common data set configurations and indicates which of the plurality of source data systems are deviating from the common data set configurations.

19. The computer-implemented method of claim 15, wherein the first data discrepancy comprises one of a missing value and an incorrect value.

20. The computer-implemented method of claim 15, wherein the first downstream system service forwards the fixed data to the one or more other downstream system services that are to receive the fixed data.

* * * * *